US00PP28199P3

(12) United States Plant Patent
Olesen

(10) Patent No.: US PP28,199 P3
(45) Date of Patent: Jul. 18, 2017

(54) COMPACT FLORIBUNDA ROSE PLANT NAMED 'POULPAL064'

(50) Latin Name: ***Rosa* hybrid**
Varietal Denomination: Poulpal064

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 12 days.

(21) Appl. No.: 14/756,254

(22) Filed: Aug. 20, 2015

(65) Prior Publication Data

US 2017/0055398 P1 Feb. 23, 2017

(51) Int. Cl.
*A01H 5/02* (2006.01)

(52) U.S. Cl.
USPC ..... Plt./146

(58) Field of Classification Search
USPC ..... Plt./141, 145, 146
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, apricot flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal064'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal064', originated as a single seedling from the stated cross.

The new variety may be distinguished from its male pollen parent and female seed parent primarily by the following characteristics. The male pollen parent has yellow flowers while the new variety has apricot flowers. The female seed parent has small flowers, about 35 cm diameter while the new variety has large flowers about 70 mm in diameter.

The objective of the hybridization of this rose variety was to create a new and distinct variety for garden use with unique qualities, such as:

1. Uniform and abundant apricot flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal064' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal064' was selected in the spring of 2008 by the inventor as a single plant from the progeny of the aforementioned hybridization.

Asexual reproduction of 'Poulpal064' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpal064' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal064'.

Specifically illustrated in FIG. 1 of the drawings are a cluster of flowers, open flowers, petals detached, sepals detached, and reproductive flower parts.

Figure 1:
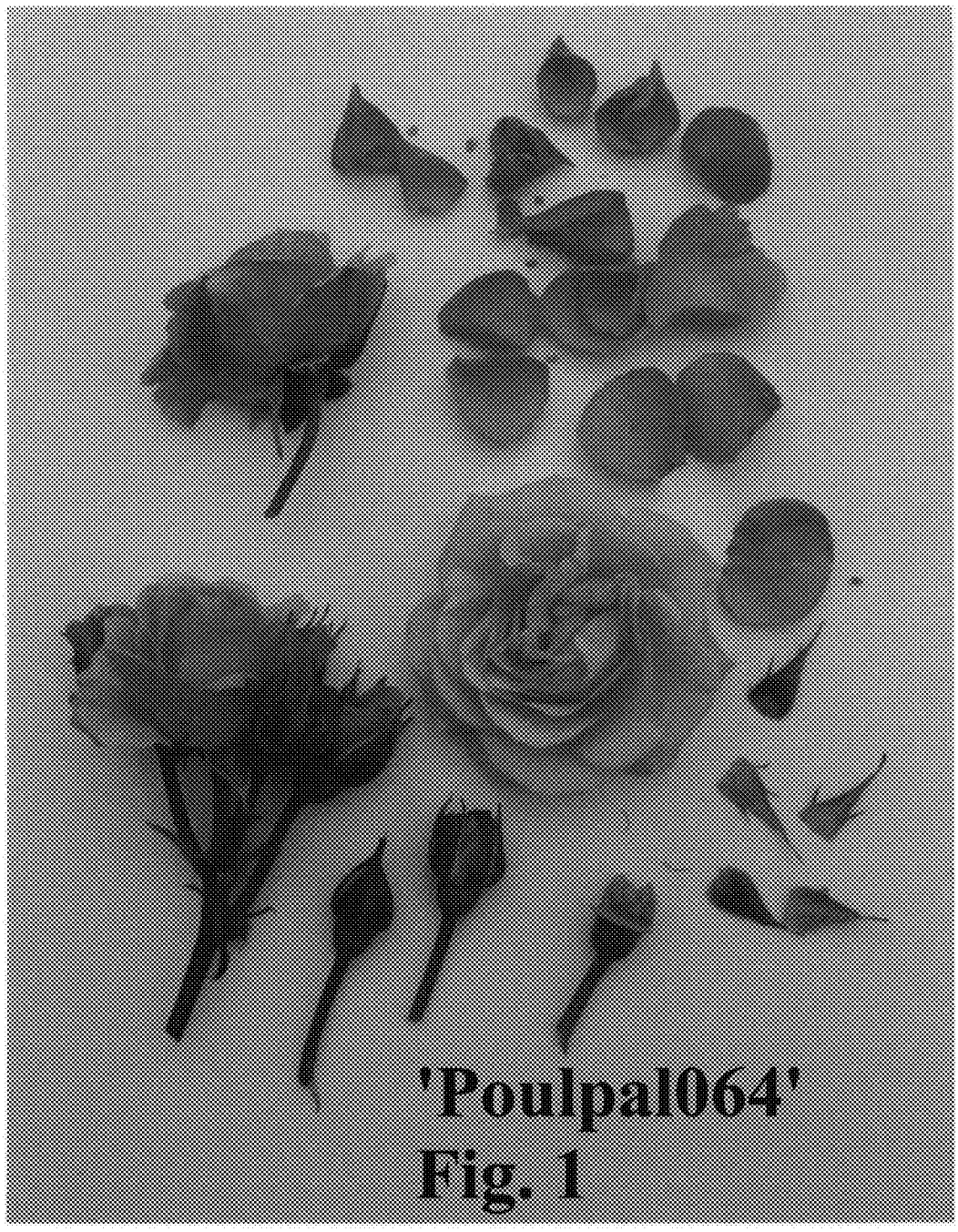
Figure 2:
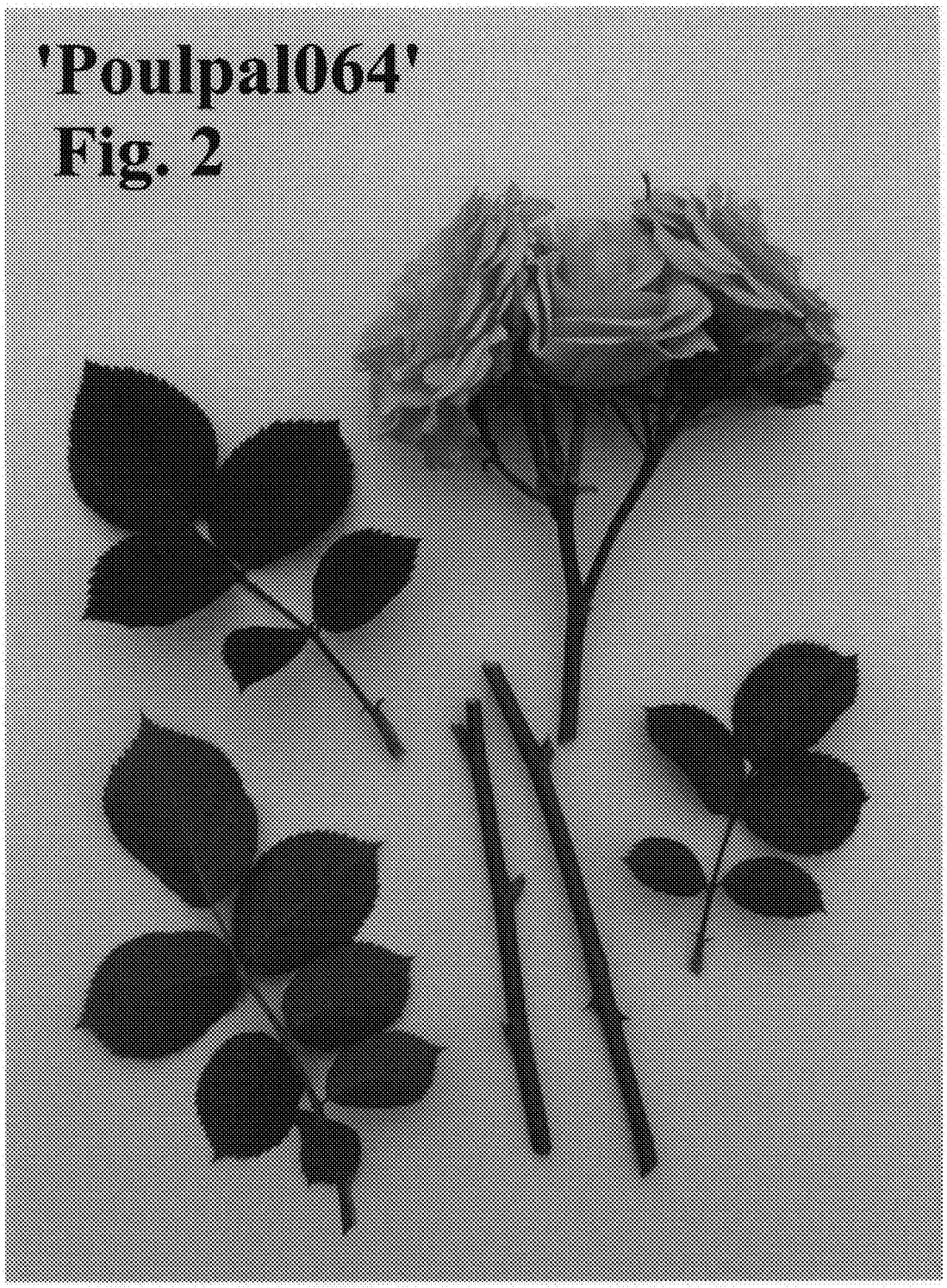

Specifically illustrated in FIG. 2 of the drawings are a cluster of open flowers, juvenile and mature leaves, and bare stems.

Plants shown are 2 years of age.

DETAILED DESCRIPTION OF THE VARIETY

The following is a description of 'Poulpal064', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulymp', U.S. Plant Pat. No. 16,744 are compared to 'Poulpal064' in Chart 1.

CHART 1

| | 'Poulpal064' | 'Poulymp' |
|---|---|---|
| Petal Count | 40 petals | 25-30 petals |
| Flower Diameter | 70 mm | 60-70 mm |
| General Tonality of Flower Color | Yellow-Orange Group 15D and Orange Group 24B | Blend of Yellow-Orange Group 20B, Orange Group 24C, and Yellow-Orange Group 21C |

Flower and Flower Bud

Blooming habit: Continuous.

Flower bud:

*Size*.—Upon opening, 28 mm in length from base of receptacle to end of bud. Bud diameter is 14 mm.

*Bud form*.—Urceolate.

*Bud color*.—As sepals divide petals are Orange-Red Group N34A, Greyed-Orange Group 172D, and Yellow Group 1B.

*Sepal inner surface*.—Color: Yellow-Green Group 146C with intonations of Greyed-Orange Group 173B. Surface: Lightly pubescent.

*Sepal outer surface*.—Color: Yellow-Green Group 146B with moderate intonations of Greyed-Purple Group 183C. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—22 mm long, 10 mm wide.

*Receptacle*.—Texture: Smooth. Size: 9 mm in height, 9 mm wide. Color: Yellow-Green Group 144A. Shape: Campanulate.

*Pedicel*.—Surface: Rough. Length: 25 to 30 mm. Diameter: 3 mm on average. Color: Yellow-Green Group 146C with intonations of Greyed-Red Group 180A. Strength: Moderate.

*Peduncle*.—Length: 5 to 7 cm. Diameter: About 4 or 5 mm. Color: Yellow-Green Group 146B with intonations of Greyed-Red Group 180A. Texture: Smooth.

Flower bud development: Flower buds are borne in panicles of about 15 flower buds per stem.

Flower bloom:

*Fragrance*.—Moderate spicy perfume.

*Duration*.—The blooms have a duration on the plant of approximately 14 days. Petals fall cleanly away from plant after flowers have fully matured.

*Size*.—Flower diameter is 70 mm when open. Flower depth is 32 mm.

*Flower shape*.—Initially high centered, semi double, with a high pointed center which is tightly closed.

*Shape of flower, side view*.—The upper portion is flattened convex. The lower portion is concave.

Petalage: Under normal conditions, flowers have 40 petals total, about 7 of which are petaloids.

General tonality of flower: Open flowers are Yellow-Orange Group 15D and Orange Group 24B.

Petal color:

Upon opening, outer petals Upper surface: Marginal zone Yellow-Orange Group 16B. Middle zone Yellow-Orange Group 22B. Basal zone Yellow Group 9A. Lower surface: Orange Group 24C with strong blended intonations of Orange-Red Group 34B. Basal zone is Yellow Group 6A.

Upon opening, inner petals: Upper surface: Orange Group 21C with basal intonations of Yellow-Orange Group 14A. Lower surface: Orange Group 29A with intonations of Yellow Group 6A at the basal zone.

After opening, outer petals Upper surface: Marginal zone is Orange-Red Group 35D. Middle zone is Orange Group 27A. Basal zone is Yellow Group 12B. Lower surface: Marginal zone is slightly Red Group 52D. Middle zone is Orange-Red Group 35B. Basal zone is Yellow Group 8A.

After opening, inner petals: Upper surface: Marginal zone is Orange-Red Group 35D with light intonations of Red Group 52D. Middle zone is Orange Group 27A. Basal zone is Yellow Group 12B. Lower surface: Marginal zone is slightly Red Group 52D. Middle zone is Orange-Red Group 35B. Basal zone is Yellow Group 8A.

Petals:

*Petal reflex*.—Lightly reflexed.

*Margin*.—Entire with occasional cleft. Weal undulations.

*Shape*.—Generally broad elliptical. Apex shape: Rounded. Base shape: Obtuse.

*Size*.—30 mm (l)×40 mm (w).

*Texture*.—Smooth.

*Thickness*.—Average.

Petaloids:

*Size*.—20 mm (l) by 15 mm (w).

*Quantity*.—About 7.

*Shape*.—Elliptical, with acute base and rounded apex.

*Color*.—Upper surface is Orange Group 21C with basal intonations of Yellow-Orange Group 14A. The lower surface is Orange Group 29A with intonations of Yellow Group 6A at the basal zone.

Reproductive flower parts:

*Pollen*.—None observed.

*Anthers*.—Size: 2 mm in length. Color: Yellow Group 11B. Quantity: 60 on average.

*Filaments*.—Color: Yellow-Orange Group 17A. Length: 5 mm.

*Pistils*.—Length: 5 mm. Quantity: 30 on average.

*Stigmas*.—Color: Greyed-Yellow Group 160A.

*Styles*.—Color: Orange-Red Group N34C.

*Location of stigmas*.—Inferior in location relative to the length of the filaments and the height of the anthers.

*Hips*.—None Observed.

Plant

Plant growth: Upright, bushy. Plants are 45 cm in height, and 45 cm wide.

Stems:

*Color*.—Juvenile growth: Yellow-Green Group 146B with Greyed-Orange Group 176B. Mature growth: Yellow-Green Group 146A.

*Length*.—On average, canes are 20 cm from the base of the plant to the flowering portion.

*Diameter*.—7 mm.

*Internodes*.—On mature canes about 40 mm between nodes.

*Surface texture*.—Young wood: Smooth. Older wood: Smooth.

Long prickles:

*Incidence*.—3 prickles per 10 cm of stem.

*Size*.—Average length of prickles on mature stems is 5 mm.

*Shape*.—Upper portion is convex. Lower portion is concave.

*Color*.—Juvenile prickles: Greyed-Red Group 179A. Mature prickles: Greyed-Red Group 179A.

Plant foliage:

*Compound leaf*.—160 mm (l)×110 (w).

*Quantity*.—2 leaves per 10 cm of stem on average.

*Color of juvenile foliage*.—Upper side: Yellow-Green Group 144A with Greyed-Purple Group 187A at margins. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 20 mm long, 7 mm wide. Quantity: 2 per compound leaf. Shape: Linear, slightly broad based with outward extending apices. Margins: Finely serrated. Color: Yellow-Green Group 144A.

*Petiole*.—Length: 40 mm. Diameter: 2 mm. *Upper surface*.—Color: Yellow-Green Group 144B with intonations of Greyed-Purple Group 184B. *Lower surface*.—Color: Yellow-Green Group 144B.

*Rachis*.—Length: 45 mm. Upper surface: Color: Yellow-Green Group 144B with intonations of Greyed-Purple Group 184A. Observations: Stipitate glands. *Lower surface*.—Color: Yellow-Green Group 144B. Observations: Small prickles.

*Leaflet*.—Quantity: Normally 5 or 7 leaflets. Margins: Serrated. Size: On average terminal leaflets are 55 mm long, 40 mm wide. Shape: Generally ovate. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal064', substantially as illustrated and described herein, due to its abundant apricot flowers, disease resistance, and extended period of bloom.

* * * * *

'Poulpal064'

'Poulpal064'